United States Patent [19]

Berner et al.

[11] Patent Number: 5,302,497
[45] Date of Patent: Apr. 12, 1994

[54] PHOTOSENSITIVE ORGANIC POLYMERIC MATERIAL CONTAINING UV ABSORBERS

[75] Inventors: Godwin Berner, Binningen, Switzerland; Andreas Valet, Eimeldingen, Fed. Rep. of Germany

[73] Assignee: Ciba-Geigy Corporation, Ardsley, N.Y.

[21] Appl. No.: 932,272

[22] Filed: Aug. 19, 1992

Related U.S. Application Data

[63] Continuation of Ser. No. 836,144, Feb. 13, 1992, abandoned, which is a continuation of Ser. No. 628,736, Dec. 17, 1990, abandoned.

[30] Foreign Application Priority Data

Dec. 21, 1989 [CH] Switzerland ............... 4594/89-0

[51] Int. Cl.$^5$ .............................. G03C 1/815
[52] U.S. Cl. .................................. 430/512; 430/931; 524/99; 524/100; 524/101; 524/102; 524/103; 524/110
[58] Field of Search .............. 430/510, 512, 931; 524/99, 100, 101, 102, 103, 110

[56] References Cited

U.S. PATENT DOCUMENTS 3,624,087 11/1971 Beck .
3,728,350 4/1973 Beck .
3,732,204 5/1973 Beck .
3,766,187 10/1973 Beck .

FOREIGN PATENT DOCUMENTS 0213925 7/1988 European Pat. Off. .
924019 4/1963 United Kingdom .

OTHER PUBLICATIONS

G. S. Puranik et al., Monatshefte Chem., 94, 410 (1963).
Chem. Absts. 110, 31366t (1989).
G. S. Puranik et al., Helv. Chem. Acta, 62, 678 (1979).
R. R. Smolders et al., Bull. Soc. Chim. Belg. 93,239 (1984).
J. Hlubucek, et al., Aust. J. Chem. 23,1881 (1970).
A. C. Jain et al., Tetrahedron, 25, 275 (1968).

Primary Examiner—Jack P. Brammer
Attorney, Agent, or Firm—William A. Teoli, Jr.

[57] ABSTRACT

Compounds of the formula

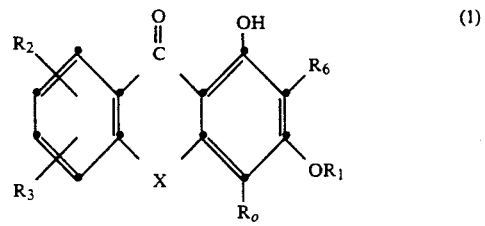

wherein $R_o$, is hydrogen or alkylene-COOR where R is alkyl or hydroxyalkyl, $R_1$ is hydrogen, alkyl, hydroxyalkyl, alkenyl or acyl, $R_2$ and $R_3$ are independently hydrogen, alkyl, alkenyl or alkoxy, $R_6$ is hydrogen or alkyl, and X is —$CH_2$—, —NH—, —S— or —O—, are suitable as UV absorbers for use in photosensitive organic materials in combination with a sterically hindered amine or hydroxyphenylbenzotriazole derivative.

12 Claims, No Drawings

PHOTOSENSITIVE ORGANIC POLYMERIC MATERIAL CONTAINING UV ABSORBERS

This application is a continuation of application Ser. No. 836,144, filed Feb. 13, 1992, which is a continuation of Ser. No. 628,736 filed Dec. 17, 1990, both now abandoned.

The present invention relates to photosensitive organic material containing novel UV absorbers, to novel thioxanthone compounds and to the use thereof as UV absorbers.

CH-A-379,760 discloses a process for the protection of photosensitive materials from the harmful effect of light, especially UV rays, wherein 1-hydroxyxanthone compounds are used. It has now been found that certain anthrones, acridones and thioxanthones can also be used successfully for this purpose.

The present invention relates to photosensitive organic material containing as UV absorber at least one compound of the formula

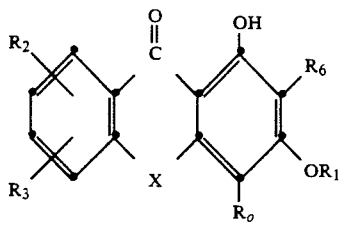

wherein X is $CH_2$, NH or S, $R_o$ is hydrogen or a radical of the formula $-(CH_2)_nCO_2R$, wherein n is 1 or 2 and R is alkyl having 1 to 18 carbon atoms or $-CH_2CH_2O)_mH$ wherein m is 1 to 12, $R_1$ is hydrogen, alkyl having 1 to 12 carbon atoms, alkyl having 2 to 18 carbon atoms which is substituted by hydroxyl and/or interrupted by oxygen, alkenyl having 2 to 12 carbon atoms or $-COR_4$, wherein $R_4$ is alkyl having 1 to 12 carbon atoms, alkenyl having 2 to 12 carbon atoms, $$-(CH_2)_y-\overset{O}{\underset{\|}{C}}R_5 \text{ or } -O-CH_2CH(OH)CH_2O-\overset{O}{\underset{\|}{C}}R_5, \text{ or}$$

$$R_1-(CH_2)_y O-\overset{O}{\underset{\|}{C}}R_5,$$

wherein $R_5$ is alkyl having 1 to 12 carbon atoms or alkenyl having 2 to 12 carbon atoms and y is 1 to 12, $R_2$ and $R_3$ independently of the other are hydrogen, alkyl having 1 to 12 carbon atoms, alkenyl having 2 to 12 carbon atoms, $-OR_1$, wherein $R_1$ is as defined, or chlorine, and $R_6$ is hydrogen or alkyl having 1 to 4 carbon atoms.

The present invention further relates to a process for the protection of photosensitive organic materials from UV radiation by using the compounds of formula (1), if desired in combination with sterically hindered amines, to thioxanthone compounds of formula (1). and to a process for their preparation.

In the compounds of formula (1) present in the materials of the invention, the substituent $R_0$ is either hydrogen or a radical of the formula $-(CH_2)_n-CO_2R$. In said formula, R is an alkyl radical having 1 to 18 carbon atoms, such as methyl, ethyl, propyl, butyl, hexyl, octyl, decyl, undecyl, dodecyl, hexadecyl and octadecyl, as well as corresponding branched isomers, or a radical of the formula $-CH_2CH_2O)_mH$, wherein m is an integer from 1 to 12. The index n is 1 or 2. Apart from hydrogen, $R_1$ is alkyl having 1 to 18 carbon atoms, for example methyl, ethyl, propyl, butyl, pentyl, hexyl, octyl, decyl, dodecyl, hexadecyl or octadecyl, corresponding branched alkyl radicals also being possible. Alkyl radicals $R_1$ having 2 to 18 carbon atoms can be substituted by one or more hydroxyl groups. They can also be interrupted by one or more oxygen atoms and, if desired, can additionally have one or more hydroxyl groups. Examples of such alkyl radicals are groupings such as $-(CH_2)_x-O-(CH_2)_yH$ and $-(CH_2)_x-O-(CH_2)_y-O-(CH_2)_zH$, the sum of x and y or of x, y and z being 2 or, respectively, 3 to 18, and

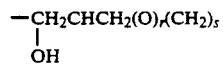

H wherein r is 0 or 1 and s is 1 to 15.

$R_1$ is also alkenyl having 2 to 12 carbon atoms, such as ethenyl, propenyl, butenyl, hexenyl, octenyl, nonenyl and dodecenyl, it also being possible for the alkenyl radicals $R_1$ to be polyunsaturated. $R_1$ can also be the corresponding branched isomers.

If $R_1$ is a radical of the formula $-COR_4$, $R_4$ is alkyl having 1 to 12 carbon atoms, alkenyl having 2 to 12 carbon atoms, examples of appropriate radicals being listed above, or else

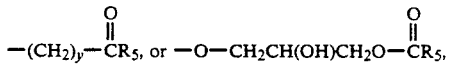

wherein $R_5$ is alkyl having 1 to 12 carbon atoms or alkenyl having 2 to 12 carbon atoms (see above for examples) and y is 1 to 12.

$R_1$ is also

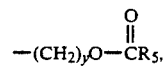

wherein $R_5$ and y are as defined.

The substituents $R_2$ and $R_3$ independently of the other are hydrogen, alkyl having 1 to 12 carbon atoms, alkenyl having 2 to 12 carbon atoms (see above for examples), $-OR_1$, wherein $R_1$ is as defined, or chlorine.

Apart from hydrogen, $R_6$ is alkyl having 1 to 4 carbon atoms, such as methyl, propyl, isopropyl, butyl or t-butyl.

The divalent group X is $CH_2$, NH or S. If the compounds of formula (1) are used in combination with sterically hindered amines or hydroxy-phenylbenzotriazole derivatives, X can additionally be 0.

In the compounds of formula (1), the substituents $R_2$ and $R_2$ are preferably hydrogen.

Other preferred compounds of formula (1) are those in which $R_0-CH_2CH_2CO_2R$ wherein R is alkyl having 1 to 18 carbon atoms or $-CH_2CH_2O)_mH$ in which m is 4 to 8, and those in which $R_0$ is a radical of the formula $-CH_2CH_2CO_2CH_3$.

In another group of compounds of formula (1) which are preferably used, the substituent $R_1$ is hydrogen, alkyl having 4 to 8 carbon atoms, alkyl having 2 to 12 carbon atoms which is substituted by hydroxyl and/or interrupted by oxygen, alkenyl having 4 to 12 carbon atoms or $-COR_4$ in which $R_4$ is alkyl having 4 to 8 carbon atoms.

Of these compounds, those in which the substituent $R_1$ is hydrogen or alkyl or alkenyl each having 4 to 8 carbon atoms are especially suitable.

It is possible to protect photosensitive organic materials from the harmful effect of UV radiation by providing these materials with a protective layer, e.g. a lacquer, which contains at least one compound of formula (1), or by incorporating such a compound into the organic material in a manner conventional per se. Combinations of such compounds of formula (1), wherein X is $CH_2$, NH, O or S, with the known light stabilizers of the sterically hindered amine type, or with hydroxyphenylbenzotriazole derivatives, can also be used successfully for this purpose.

Examples of the wide variety of photosensitive organic materials which can be protected according to the invention from the harmful effect of light are:

1. Polymers of monoolefins and diolefins, for example polypropylene, polyisobutylene, polybutlene, polymethylpentlene, polyisoprene or polybutadiene, as well as polymers of cycloolefins, e.g. of cyclopentene or norbornene, and polyethylene (which can be uncrosslinked or cross-linked), e.g. high density polyethylene (HDPE), low density polyethylene (LDPE) and linear low density polyethylene (LLDPE).

2. Mixtures of the polymers mentioned under 1), e.g. mixtures of polypropylene with polyisobutylene and of polypropylene with polyethylene (e.g. PP/HDPE, PP/LDPE) and mixtures of different types of polyethylene (e.g. LDPE/HDPE).

3. Copolymers of monoolefins and diolefins with each other or with other vinyl monomers, e.g. ethylene/propylene copolymers, linear low density polyethylene (LLDPE) and mixtures thereof with low density polyethylene (LDPE), propylene/but-1-ene copolymers, propylene/isobutylene copolymers, etbylene/but-1-ene copolymers, etbylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned under 1), e.g. polypropylene-ethylene/propylene copolymers, LDPE-ethylene/vinyl acetate copolymers, LDPE-ethylene/acrylic acid copolymers, LLDPE-ethylene/vinyl acetate copolymers and LLDPE-etbylene/acrylic acid copolymers.

3a. Hydrocarbon resins (e.g. $C_5$–$C_9$), including hydrogenated modifications thereof (e.g. tackifiers).

4. Polystyrene, poly(p-methylstyrene) and poly(α-methylstyrene).

5. Copolymers of styrene or α-methylstyrene with dienes or acrylic derivatives, e.g. styrene/butadiene, styrene/acrylonitrile, styrene/alkyl methacrylate, styrene/butadiene/alkyl acrylate, styrene/maleic anhydride and styrene/acrylonitrile/methyl acrylate; high-impact mixtures of styrene copolymers and another polymer, e.g. a polyacrylate, a diene polymer or an ethylene/propylene/diene terpolymer; and block copolymers of styrene, e.g. styrene/butadiene/styrene, styrene/isoprene/styrene, styrene/ethylene-butylene/styrene or styrene/ethylene-propylene/styrene.

6. Graft copolymers of styrene or a-methylstyrene, e.g. styrene on polybutadiene; styrene on polybutadiene/styrene or polybutadiene/acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene; styrene and acrylonitrile on ethylene/propylene/diene terpolymers; styrene and acrylonitrile on polyalkyl acrylates or polyalkyl methacrylates; and styrene and acrylonitrile on acrylate/butadiene copolymers, as well as mixtures thereof with the copolymers mentioned under 5), e.g. the mixtures known as ABS, MBS, ASA or AES polymers.

7. Halogenated polymers such as polychloroprene, chlorinated rubber, chlorinated or sulfochlorinated polyethylene, copolymers of ethylene and chlorinated ethylene, and epichlorohydrin homopolymers and copolymers, and especially polymers of balogenated vinyl compounds, e.g. polyvinyl chloride, polyvinylidene chloride, polyvinyl fluoride and polyvinylidene fluoride; as well as copolymers thereof, such as vinyl chloride/vinylidene chloride, vinyl chloride/vinyl acetate or vinylidene chloride/vinyl acetate.

8. Polymers derived from α,β-unsaturated acids and derivatives thereof, such as polyacrylates and polymethacrylates, polyacrylamides and polyacrylonitriles.

9. Copolymers of the monomers mentioned under 8) with each other or with other unsaturated monomers, e.g. acrylonitrile/butadiene copolymers, acrylonitrile/alkyl acrylate copolymers, acrylonitrile/alkoxyalkyl acrylate copolymers or acrylonitrile/vinyl halide copolymers, or acrylonitrile/alkyl methacrylate/butadiene terpolymers.

10. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine; as well as copolymers thereof with olefins mentioned in section 1.

11. Homopolymers and copolymers of cyclic ethers, such as polyalkylene glycols, polyethylene oxide, polypropylene oxide or copolymers thereof with bisglycidyl ethers.

12. Polyacetals such as polyoxymethylene, and polyoxymethylenes containing comonomers, e.g. ethylene oxide; and polyacetals modified with thermoplastic polyurethanes, acrylates or MBS.

13. Polyphenylene oxides and sulfides and mixtures thereof with styrene polymers or polyamides.

14. Polyurethanes derived from polyethers, polyesters and polybutadienes with terminal hydroxyl groups on the one hand and from aliphatic or aromatic polyisocyanates on the other, as well as precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, and aromatic polyamides obtained from m-xylene, diamine and adipic acid; polyamides prepared from hexamethylenediamine and isophthalic and/or terephthalic acid and, if desired, an elastomer as modifier, e.g. poly-2,4,4-trimethylhexamethylene terephtbalamide or poly-m-phenylene isophthalamide; block copolymers of the aforementioned polyamides with polyolefins, olefin copolymers, ionomers or chemically bonded or grafted elastomers, or with polyethers, e.g. with polyethylene glycol, polypropylene glycol or polytetramethylene glycol; and also polyamides or copolyamides modified with EPDM or ABS, and polyamides condensed during processing ("RIM polyamide systems").

16. Polyureas, polyimides, polyamide-amides and polybenzimidazoles.

17. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terepbthalate and polyhydroxybenzoates, as well as block polyether-esters derived from hydroxyl-terminated polyethers; and also polyesters modified with polycarbonates or MBS.

18. Polycarbonates and polyester-carbonates.

19. Polysulfones, polyether-sulfones and polyetherketones.

20. Crosslinked polymers derived from aldehydes on the one hand and phenols, urea or melamine on the other, such as phenol/formaldehyde resins, urea/formaldehyde resins and melamine/formaldehyde resins.

21. Drying and non-drying alkyd resins.

22. Unsaturated polyester resins derived from copolyesters of saturated and unsaturated dicarboxylic acids with polyhydric alcohols, and vinyl compounds as crosslinking agents, and also halogenated modifications thereof of low flammability.

23. Crosslinkable acrylic resins derived from substituted acrylic acid esters, e.g. from epoxy acrylates, urethane acrylates or polyester acrylates.

24. Alkyd resins, polyester resins and acrylate resins crosslinked with melamine resins, urea resins, polyisocyanates or epoxy resins.

25. Crosslinked epoxy resins derived from polyepoxides, e.g. from bisglycidyl ethers or from cycloaliphatic diepoxides.

26. Natural polymers such as cellulose, natural rubber and gelatin, and derivatives thereof chemically modified in a polymer-homologous manner, such as cellulose acetates, cellulose propionates and celluiose butyrates, or the cellulose ethers, such as methyl cellulose; and rosins and derivatives.

27. Mixtures (polyblends) of the aforementioned polymers, e.g. PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 66 and copolymers, PA/HDPE, PA/PP and PA/PPO.

Examples of hindered amines which can be used in combination with the compounds of formula (1), wherein X is $CH_2$, NH, O or S, are polyalkylpiperidine compounds containing at least one group of the formula

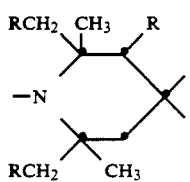

wherein R is hydrogen or methyl. R is preferably hydrogen. Said compounds are derivatives of polyalkyl-piperidines, especially of 2,2,6,6-tetra-methylpiperidine. These compounds preferably carry one or two polar substituents or a polar spiro ring system in the 4-position of the piperidine ring. Said compounds can be low-molecular or oligomeric or polymeric compounds.

The following classes of polyalkylpiperidines are of particular importance:

a) Compounds of formula III

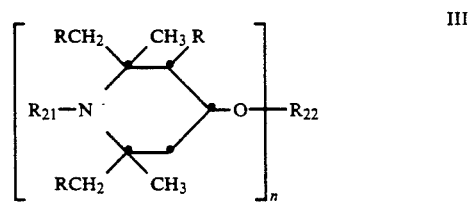

wherein n is a number from 1 to 4, preferably 1 or 2, R is hydrogen or methyl, $R_{21}$ is hydrogen, oxyl, hydroxyl, $C_1$–$C_{12}$ alkyl, $C_3$–$C_8$ alkenyl, $C_3$–$C_8$ alkynyl, $C_7$–$C_{12}$ aralkyl, $C_1$–$C_{18}$ alkoxy, $C_5$–$C_8$ cycloalkoxy, $C_7$–$C_9$ phenylalkoxy, $C_1$–$C_8$ alkanoy, $C_3$–$C_5$ alkenoyl, $C_1$–$C_{18}$ alkanoyloxy, benzyloxy, glycidyl or a group —$CH_2C$-H(OH)—Z, wherein Z is hydrogen, methyl or phenyl, $R_{21}$ preferably being H, $C_1$–$C_4$ alkyl, allyl, benzyl, acetyl or acryloyl, and $R_{22}$ when n is 1 is hydrogen, $C_1$–$C_{18}$ alkyl which may be interrupted by one or more oxygen atoms, cyanoethyl, benzyl, glycidyl, a monovalent radical of an aliphatic, cycloaliphatic, araliphatic, unsaturated or aromatic carboxylic acid, carbamic acid or phosphorus-containing acid, or a monovalent silyl radical, preferably a radical of an aliphatic carboxylic acid having 2 to 18 C atoms, of a cycloaliphatic carboxylic acid having 7 to 15 C atoms, of an $\alpha,\beta$-unsaturated carboxylic acid having 3 to 5 C atoms or of an aromatic carboxylic acid having 7 to 15 C atoms, $R_{22}$ when n is 2 is $C_1$–$C_{12}$ alkylene, $C_4$–$C_{12}$ alkenylene, xylylene, a divalent radical of an aliphatic, cycloaliphatic, araliphatic or aromatic dicarboxylic acid, dicarbamic acid or phosphorus-containing acid, or a divalent silyl radical, preferably a radical of an aliphatic dicarboxylic acid having 2 to 36 C atoms, of a cycloaliphatic or aromatic dicarboxylic acid having 8–14 C atoms or of an aliphatic, cycloaliphatic or aromatic dicarbamic acid having 8–14 C atoms, $R_{22}$ when n is 3 is a trivalent radical of an aliphatic, cycloaliphatic or aromatic tricarboxylic acid, of an aromatic tricarbamic acid or of a phosphorus-containing acid, or a trivalent silyl radical, and $R_{22}$ when n is 4 is a tetravalent radical of an aliphatic, cycloaliphatic or aromatic tetracarboxylic acid.

Any $C_1$–$C_{12}$ alkyl substituents are e.g. methyl, ethyl, n-propyl, n-butyl, sec-butyl, tert-butyl, n-hexyl, n-octyl, 2-ethylhexyl, n-nonyl, n-decyl, n-undecyl or n-dodecyl.

$R_{21}$ or $R_{22}$ as $C_1$–$C_{18}$ alkyl can be e.g. the groups listed above and additionally n-tridecyl, n-tetradecyl, n-hexadecyl or n-octadecyl, for example.

$R_{21}$ as $C_3$–$C_8$ alkenyl can be e.g. prop-1-enyl, allyl, methallyl, but-2-enyl, pent-2-enyl, bex-2-enyl, oct-2-enyl or 4-tert-butylbut-2-enyl.

$R_{21}$ as $C_3$–$C_8$ alkynyl is preferably propargyl.

$R_{21}$ as $C_7$–$C_{12}$ aralkyl is especially phenethyl and in particular benzyl.

$R_{21}$ as $C_1$–$C_8$ alkanoyl is, for example, formyl, propionyl, butyryl or octanoyl, but preferably acetyl, and $R_{21}$ as $C_3$–$C_5$ alkenoyl is especially acryloyl.

R$_{21}$ as C$_1$–C$_{18}$ alkoxy is e.g. hexyloxy, heptyloxy, octyloxy or decyloxy. R$_{21}$ as cycloalkoxy is preferably cyclohexyloxy. R$_{21}$ as phenylalkoxy is preferably benzyloxy. R$_{21}$ as alkanoyloxy is e.g. acetoxy, butyroyloxy, hexanoyloxy, octanoyloxy, decanoyloxy or stearoyloxy.

R$_{22}$ as a monovalent radical of a carboxylic acid is, for example, an acetic acid, caproic acid, stearic acid, acrylic acid, methacrylic acid, benzoic acid or β-(3,5-di-tert-butyl-4-hydroxyphenyl)propionic acid radical.

R$_{22}$ as a divalent radical of a dicarboxylic acid is, for example, a malonic acid, succinic acid, glutaric acid, adipic acid, suberic acid, sebacic acid, maleic acid, itaconic acid, phthalic acid, dibutylmalonic acid, dibenzylmalonic acid, butyl(3,5-di-tert-butyl-4-hydroxybenzyl)malonic acid or bicycloheptenedicarboxylic acid radical.

R$_{22}$ as a trivalent radical of a tricarboxylic acid is e.g. a trimellitic acid, citric acid or nitrilotriacetic acid radical.

R$_{22}$ as a tetravalent radical of a tetracarboxylic acid is e.g. the tetravalent radical of butane-1,2,3,4-tetracarboxylic acid or of pyromellitic acid.

R$_{22}$ as a divalent radical of a dicarbamic acid is, for example, a hexamethylenedicarbamic acid or 2,4-toluylenedicarbamic acid radical.

Preferred compounds of formula III are those in which R is hydrogen, R$_{21}$ is hydrogen or methyl, n is 1 and R$_{22}$ is C$_1$–C$_{18}$ alkyl or n is 2 and R$_{22}$ is the diacyl radical of an aliphatic dicarboxylic acid having 4–12 C atoms.

The following compounds are examples of polyalkylpiperidine compounds of this class:

1) 4-hydroxy-2,2,6,6-tetramethylpiperidine
2) 1-allyl-4-hydroxy-2,2,6,6-tetramethylpiperidine
3) 1-benzyl-4-hydroxy-2,2,6,6-tetramethylpiperidine
4) 1-(4-tert-butylbut-2-enyl)-4-hydroxy-2,2,6,6-tetramethylpiperidine
5) 4-stearoyloxy-2,2,6,6-tetramethylpiperidine
6) 1-ethyl-4-salicyloyloxy-2,2,6,6-tetramethylpiperidine
7) 4-methacryloyloxy-1,2,2,6,6-pentamethylpiperidine
8) 1,2,2,6,6-pentamethylpiperidine-4-yl β-(3,5-di-tert-butyl-4-hydroxy-phenyl)propionate
9) di(1-benzyl-2,2,6,6-tetramethylpiperidine-4-yl) maleate
10) di(2,2,6,6-tetramethylpiperidin-4-yl) succinate
11) di(2,2,6,6-tetramethylpiperidin-4-yl) glutarate
12) di(2,2,6,6-tetramethylpiperidin-4-yl) adipate
13) di(2,2,6,6-tetramethylpiperidin-4-yl) sebacate
14) di(1,2,2,6,6-pentamethylpiperidine-4-yl) sebacate
15) di(1,2,3,6-tetramethyl-2,6-diethylpiperidin-4-yl) sebacate
16) di(1-allyl-2,2,6,6-tetramethylpiperidin-4-yl) phthalate
17) 1-hydroxy-4-β-cyanoethyl-2,2,6,6-tetramethylpiperidine
18) 1-acetyl-2,2,6,6-tetramethylpiperidin-4-yl acetate
19) tri(2,2,6,6-tetramethylpiperidin-4-yl) trimellitate
20) 1-acryloyl-4-benzyloxy-2,2,6,6-tetramethylpiperidine
21) di(2,2,6,6-tetramethylpiperidin-4-yl) diethylmalonate
22) di(1,2,2,6,6-pentamethylpiperidin-4-yl) dibutylmalonate
23) di(1,2,2,6,6-pentamethylpiperidin-4-yl) butyl(3,5-di-tert-butyl-4-hydroxybenzyl)malonate
24) di(1-octyloxy-2,2,6,6-tetramethylpiperidin-4-yl) sebacate
25) di(1-cyclohexyloxy-2,2,6,6-tetramethylpiperidin-4-yl) sebacate
26) hexane-1',6'-bis(4-carbamoyloxy-1-n-butyl-2,2,6,6-tetramethylpiperidine)
27) toluene-2',4'-bis(4-carbamoyloxy-1-n-propyl-2,2,6,6-tetramethylpiperidine)
28) tetra(2,2,6,6-tetramethylpiperidin-4-yl) butane-1,2,3,4-tetracarboxylate
29) tetra(1,2,2,6,6-pentamethylpiperidin-4-yl) butane-1,2,3,4-tetracarboxylate
30) tris(1-propyl-2,2,6,6-tetramethylpiperidin-4-yl) phosphite
31) tris(1-propyl-2,2,6,6-tetramethylpiperidin-4-yl) phosphate
32) phenyl[bis(1,2,2,6,6-pentamethylpiperidin-4-yl)] phosphonate
33) 4-hydroxy-1,2,2,6,6-pentamethylpiperidine
34) 4-hydroxy-N-hydroxyethyl-2,2,-6,6-tetramethylpiperidine
35) 4-hydroxy-N-(2-hydroxypropyl)-2,2,6,6-tetramethylpiperidine
36) 1-glycidyl-4-hydroxy-2,2,6,6-tetramethylpiperidine b) Compounds of formula IV,

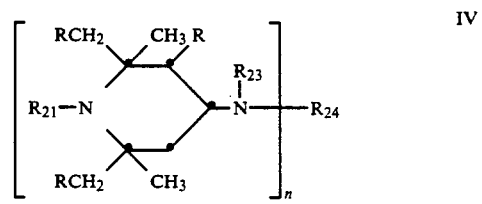

IV wherein n is the number 1 or 2, R and R$_{21}$ are as defined under a), R$_{23}$ is hydrogen, C$_1$–C$_{12}$ alkyl, C$_2$–C$_5$ hydroxyalkyl, C$_5$–C$_7$ cycloalkyl, C$_7$–C$_8$ aralkyl, C$_2$–C$_{18}$ alkanoyl, C$_3$–C$_5$ alkenoyl, benzoyl or a group of the formula

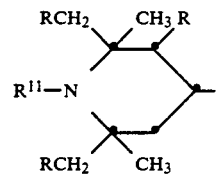

and R$_{24}$ when n is 1 is hydrogen, C$_1$–C$_{18}$ alkyl, C$_3$–C$_8$ alkenyl, C$_5$–C$_7$ cycloalkyl, C$_1$–C$_4$ alkyl substituted by a hydroxyl, cyano, alkoxycarbonyl or carbamide group, glycidyl or a group of the formula —CH$_2$—CH(OH)—Z or of the formula —CONH—Z, wherein Z is hydrogen, methyl or phenyl, R$_{24}$ when n is 2 is C$_2$–C$_{12}$ alkylene, C$_6$–C$_{12}$ arylene, xylylene, a group —CH$_2$—CH(OH)—CH$_2$— or a group —CH$_2$—CH(OH)—CH$_2$—O—D—O—, wherein D is C$_2$–C$_{10}$ alkylene, C$_6$–C$_{15}$ arylene or C$_6$–C$_{12}$ cycloalkylene, or, provided that R$_{23}$ is not alkanoyl, alkenoyl or benzoyl, R$_{24}$ can also be a divalent radical of an aliphatic, cycloaliphatic or aromatic dicarboxylic acid or dicarbamic acid or the group —CO—, or R$_{23}$ and R$_{24}$ together, when n is 1, can be the divalent radical of an aliphatic, cycloaliphatic or aromatic 1,2- or 1,3-dicarboxylic acid.

Any C$_1$–C$_{12}$ or C$_1$–C$_{18}$ alkyl substituents are as already defined under a).

Any C$_5$–C$_7$ cycloalkyl substituents are especially cyclohexyl.

$R_{23}$ $C_7$–$C_8$ aralkyl is especially phenylethyl or in particular benzyl. $R_{23}$ as $C_2$–$C_5$ hydroxyalkyl is especially 2-hydroxyethyl or 2-hydroxypropyl.

$R_{23}$ as $C_2$–$C_{18}$ alkanoyl is, for example, propionyl, butyryl, octanoyl, dodecanoyl, hexadecanoyl or octadecanoyl, but preferably acetyl, and $R_{23}$ as $C_3$–$C_5$ alkenoyl is especially acryloyl.

$R_{24}$ as $C_2$–$C_8$ alkenyl is e.g. allyl, methallyl, but-2-enyl, pent-2-enyl, hex-2-enyl or oct-2-enyl.

$R_{24}$ as $C_1$–$C_4$ alkyl substituted by a hydroxyl, cyano, alkoxycarbonyl or carbamide group can be e.g. 2-hydroxyethyl, 2-hydroxypropyl, 2-cyanoethyl, methoxycarbonylmethyl, 2-ethoxycarbonylethyl, 2-aminocarbonylpropyl or 2-(dimethylaminocarbonyl)ethyl.

Any $C_2$–$C_{12}$ alkylene substituents are e.g. ethylene, propylene, 2,2-dimethylpropylene, tetramethylene, hexamethylene, octamethlene, decamethylene or dodecamethylene.

Any $C_6$–$C_{15}$ arylene substituents are e.g. o-, m- or p-phenylene, 1,4-naphthalene or 4,4′-diphenylene.

D as $C_6$–$C_{12}$ cycloalkylene is especially cyclohexylene.

Preferred compounds of formula IV are those in which n is 1 or 2, R is hydrogen, $R_{21}$ is hydrogen or methyl, $R_{23}$ is hydrogen, $C_1$–$C_{12}$ alkyl or a group of the formula

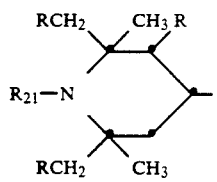

and $R_{24}$ in the case where n=1 is hydrogen or $C_1$–$C_{12}$ alkyl and in the case where n=2 is $C_2$–$C_8$ alkylene.

The following compounds are examples of polyalkylpiperidine compounds of this class:

37) N,N′-bis(2,2,6,6-tetramethylpiperidin-4-yl)hexamethylene-1,6-diamine
38) N,N′-bis(2,2,6,6-tetramethylpiperidin-4-yl)hexamethylene-1,6-diacetamide
39) bis(2,2,6,6-tetramethylpiperidin-4-yl)amine
40) 4-benzoylamino-2,2,6,6-tetramethylpiperidine
41) N,N′-bis(2,2,6,6-tetramethylpiperidin-4-yl)-N,N′-dibutyladipamide
42) N,N′-bis(2,2,6,6-tetramethylpiperidin-4-yl)-N,N′-dicyclohexyl-2-hydroxypropylene -1,3-diamine
43) N,N′-bis(2,2,6,6-tetramethylpiperidin-4-yl)-p-xylylenediamine
44) N,N′-bis(2,2,6,6-tetramethylpiperidin-4-yl)succindiamide
45) di(2,2,6,6-tetramethylpiperidin-4-yl) N-(2,2,6,6-tetramethylpiperidin -4-yl)-β-aminodipropionate
46) the compound of the formula

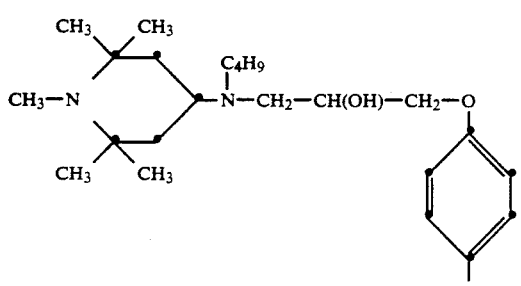

47) 4-(bis-2-hydroxyethylamino)-1,2,2,6,6 -pentamethylpiperidine
48) 4-(3-methyl-4-hydroxy-5-tert-butylbenzamido)-2,2,6,6-tetramethylpiperidine
49) 4-methacrylamido-1,2,2,6,6-pentamethylpiperidine c) Compounds of formula V,

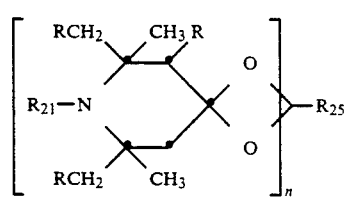

wherein n is the number 1 or 2, R and $R_{21}$ are as defined under a) and $R_{25}$ when n is 1 is $C_2$–$C_8$ alkylene, $C_2$–$C_8$ hydroxyalkylene or $C_4$–$C_{22}$ acyloxyalkylene and when n is 2 is the group (—$CH_2$)$_2$C($CH_2$—)$_2$.

$R_{25}$ as $C_2$–$C_8$ alkylene or $C_2$–$C_8$ hydroxyalkylene is, for example, ethylene, 1-metbylethylene, propylene, 2-ethylpropylene or 2-ethyl-2-hydroxymethylpropylene.

$R_{25}$ as $C_4$–$C_{22}$ acyloxyalkylene is e.g. 2-ethyl-2-acetoxymethylpropylene.

The following compounds are examples of polyalkylpiperidine compounds of this class:

50) 9-aza-8,8,10,10-tetramethyl-1,5-dioxaspiro[5.5]undecane
51) 9-aza-8,8,10,10-tetramethyl-3-ethyl-1,5-dioxaspiro[5.5]undecane
52) 8-aza-2,7,7,8,9,9-hexamethyl-1,4-dioxaspiro[4.5]decane
53) 9-aza-3-hydroxymethyl-3-ethyl-8,8,9,10,10-pentamethyl-1,5-dioxaspiro [5.5]undecane
54) 9-aza-3-ethyl-3-acetoxymethyl-9-acetyl-8,8,10,10-tetramethyl-1,5-dioxaspiro [5.5]undecane
55) 2,2,6,6-tetramethylpiperidine-4-spiro-2′-(1′,3′-dioxane)-5′-spiro-5″-(1″,3″-dioxane)-2″- spiro-4‴-(2‴,2‴,6‴,6‴-tetramethylpiperidine)

d) Compounds of formulae VIA, VIB and VIC

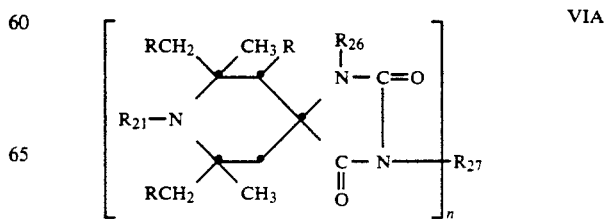

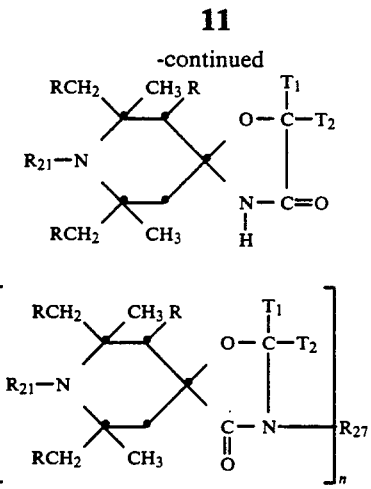

wherein n is the number 1 or 2, R and $R_{21}$ are as defined under a), $R_{26}$ is hydrogen, $C_1$-$C_{12}$ alkyl, allyl, benzyl, glycidyl or $C_2$-$C_6$ alkoxyalkyl, $R_{27}$ when n is 1 is hydrogen, $C_1$-$C_{12}$ alkyl, $C_3$-$C_5$ alkenyl, $C_7$-$C_9$ aralkyl, $C_5$-$C_7$ cycloalkyl, $C_2$-$C_4$ hydroxyalkyl, $C_2$-$C_6$ alkoxyalkyl, $C_6$-$C_{10}$ aryl, glycidyl or a group of the formula —($CH_2$)$_p$—COO—Q or of the formula —($CH_2$)$_p$—O—CO—Q, wherein p is 1 or 2 and Q is $C_1$-$C_4$ alkyl or phenyl, and $R_{27}$ when n is 2 is $C_2$-$C_{12}$ alkylene, $C_4$-$C_{12}$ alken $C_6$-$C_{12}$ arylene, a group —$CH_2$—CH(OH)—CH$_2$—O—D—O—$CH_2$—CH(OH)—$CH_2$—, wherein D is $C_2$-$C_{10}$ alkylene, $C_6$-$C_{15}$ arylene or $C_6$-$C_{12}$ cycloalkylene, or a group —$CH_2$CH(OZ')$CH_2$—(O$CH_2$—CH(OZ')$CH_2$)$_2$—, wherein Z' is hydrogen, $C_1$-$C_{18}$ alkyl, allyl, benzyl, $C_2$-$C_{12}$ alkanoyl or benzoyl, and $T_1$ and $T_2$ independently of the other are hydrogen, $C_1$-$C_{18}$ alkyl or $C_6$-$C_{10}$ aryl or $C_7$-$C_9$ aralkyl which is unsubstituted or substituted by halogen or $C_1$-$C_4$ alkyl, or $T_1$ and $T_2$ form a $C_5$-$C_{12}$ cycloalkane ring together with the C atom to which they are bonded.

Any $C_1$-$C_{12}$ alkyl substituents are e.g. methyl, ethyl, n-propyl, n-butyl, sec-butyl, tert-butyl, n-hexyl, n-octyl, 2-ethylhexyl, n-nonyl, n-decyl, n-undecyl or n-dodecyl.

Any $C_1$-$C_{18}$ alkyl substituents can be e.g. the groups listed above and additionally n-tridecyl, n-tetradecyl, n-hexadecyl or n-octadecyl, for example.

Any $C_2$-$C_6$ alkoxyalkyl substituents are e.g. methoxymethyl, ethoxymethyl, propoxymethyl, tert-butoxymethyl, ethoxyethyl, ethoxypropyl, n-butoxy-ethyl, tert-butoxyethyl, isopropoxyethyl or propoxypropyl.

$R_{27}$ as $C_3$-$C_5$ alkenyl is e.g. prop-1-enyl, allyl, methallyl, but-2-enyl or pent-2-enyl.

$R_{27}$, $T_1$ and $T_2$ as $C_7$-$C_9$ aralkyl are especially phenethyl or in particular benzyl. If $T_1$ and $T_2$ form a cycloalkane ring together with the C atom, said ring can be e.g. a cyclopentane, cyclohexane, cyclooctane or cyclododecane ring.

$R_{27}$ as $C_2$-$C_4$ hydroxyalkyl is e.g. 2-hydroxyethyl, 2-hydroxypropyl, 2-hydroxybutyl or 4-hydroxybutyl.

$R_{27}$, $T_1$ and $T_2$ as $C_6$-$C_{10}$ aryl are especially phenyl or α- or β-naphthyl which are unsubstituted or substituted by halogen or $C_1$-$C_4$ alkyl.

$R_{27}$ as $C_2$-$C_{12}$ alkylene is e.g. ethylene, propylene, 2,2-dimethylpropylene, tetramethylene, hexamethylene, octamethylene, decamethylene or dodecamethylene.

$R_{27}$ as $C_4$-$C_{12}$ alkenylene is especially but-2-ethylene, pent-2-ethylene or hex-3-ethylene.

$R_{27}$ as $C_6$-$C_{12}$ arylene is, for example, o-, m- or p-phenylene, 1,4-naphthylene or 4,4'-diphenylene.

Z' as $C_2$-$C_{12}$ alkanoyl is, for example, propionyl, butyryl, octanoyl or dodecanoyl, but preferably acetyl.

D as $C_2$-$C_{10}$ alkylene, $C_6$-$C_{15}$ arylene or $C_6$-$C_{12}$ cycloalkylene is as defined under b).

The following compounds are examples of polyalkylpiperidine compounds of this class:

56) 3-benzyl-1,3,8-triaza-7,7,9,9-tetramethylspiro[4.5]-decane-2,4-dione
57) 3-n-octyl-1,3,8-triaza-7,7,9,9-tetramethylspiro[4.5]-decane-2,4-dione
58) 3-allyl-1,3,8-triaza-1,7,7,9,9-pentamethylspiro[4.5]-decane-2,4-dione
59) 3-glycidyl-1,3,8-triaza-7,7,8,9,9-pentamethylspiro[4.5]decane-2,4-dione
60) 1,3,7,7,8,9,9-heptamethyl-1,3,8-triazaspiro[4.5]decane-2,4-dione
61) 2-isopropyl-7,7,9,9-tetramethyl-1-oxa-3,8-diaza-4-oxospiro[4.5]decane
62) 2,2-dibutyl-7,7,9,9-tetramethyl-1-oxa-3,8-diaza-4-oxospiro[4.5]decane
63) 2,2,4,4-tetramethyl-7-oxa-3,20-diaza-21-oxodispiro[5.1.11.2]-heneicosane
64) 2-butyl-7,7,9,9-tetramethyl-1-oxa-4,8-diaza-3-oxospiro[4.5]decane
65) 8-acetyl-3-dodecyl-1,3,8-triaza-7,7,9,9-tetramethylspiro[4.51-decane-2,4-dione or the compounds of the following formulae:

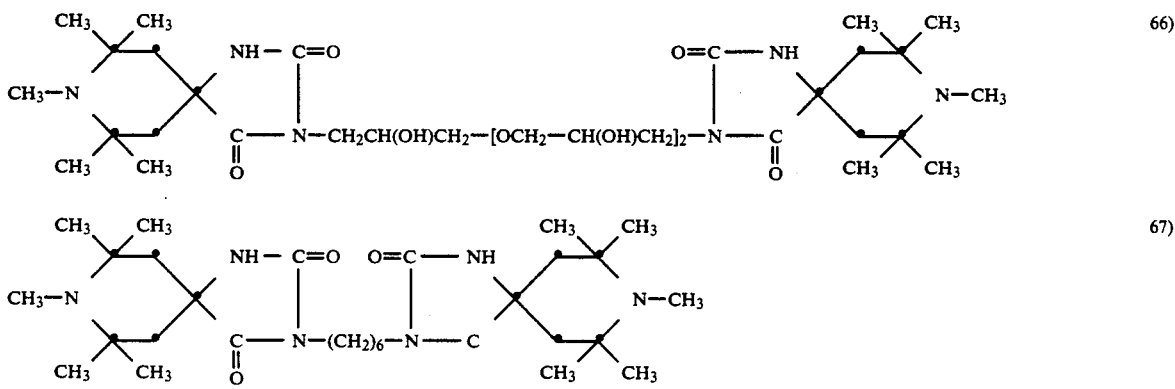

-continued

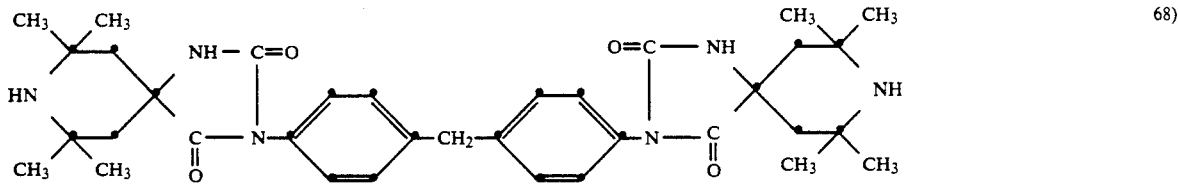
68)

69)

e) Compounds of formula VII,

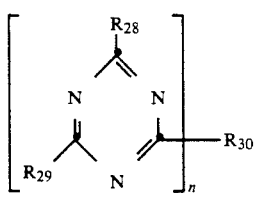
VII wherein n is the number 1 or 2, $R_{28}$ is a group of the formula

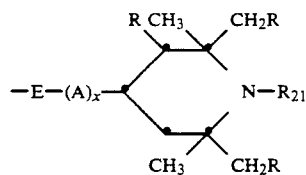

wherein R and $R_{21}$ are as defined under a), E is —O— or —$NR_{21}$—, A is $C_2$-$C_6$ alkylene or —$(CH_2)_3$—O— and x is the number 0 or 1, $R_{29}$ is the same as $R_{28}$ or is one of the groups —$NR_{31}R_{32}$, —$OR_{33}$, —$NHCH_2OR_{33}$ and —$N(CH_2OR_{33})_2$, $R_{30}$ when n=1 is the same as $R_{28}$ or $R_{29}$ and when n=2 is a group —E—B—E—, wherein B is $C_2$-$C_6$ alkylene which may be interrupted by —$N(R_{31})$—, $R_{31}$ is $C_1$-$C_{12}$ alkyl, cyclohexyl, benzyl, $C_1$-$C_4$ hydroxyalkyl or a group of the formula

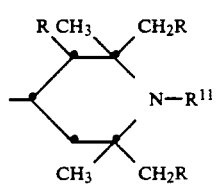

$R_{32}$ is $C_1$-$C_{12}$ alkyl, cyclohexyl, benzyl or $C_1$-$C_4$ hydroxyalkyl and $R_{33}$ is hydrogen, $C_1$-$C_{12}$ alkyl or phenyl, or $R_{31}$ and $R_{32}$ together are $C_4$-$C_5$ alkylene or $C_4$-$C_5$ oxaalkylene, for example

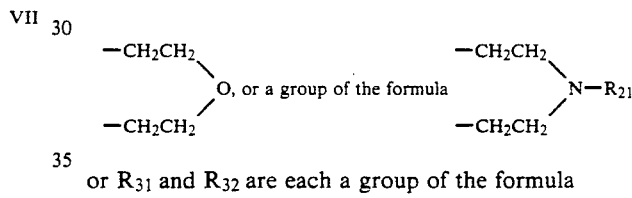

or $R_{31}$ and $R_{32}$ are each a group of the formula

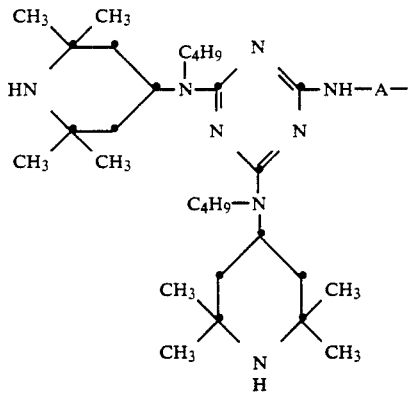

Any $C_1$-$C_{12}$ alkyl substituents are, for example, methyl, ethyl, n-propyl, n-butyl, sec-butyl, tert-butyl, n-hexyl, n-octyl, 2-ethylhexyl, n-nonyl, n-decyl, n-undecyl or n-dodecyl.

Any $C_1$-$C_4$ hydroxyalkyl substituents are e.g. 2-hydroxyethyl, 2-hydroxypropyl, 3-hydroxypropyl, 2-hydroxybutyl or 4-hydroxybutyl.

A as $C_2$-$C_6$ alkylene is, for example, ethylene, propylene, 2,2-dimethylpropylene, tetramethylene or hexamethylene.

If $R_{31}$ and $R_{32}$ together are $C_4$-$C_5$ alkylene or $C_4$-$C_5$ oxaalkylene, this is e.g. tetramethylene, pentamethylene or 3-oxapentamethylene.

The compounds of the following formulae are examples of polyalkylpiperidine compounds of this class:

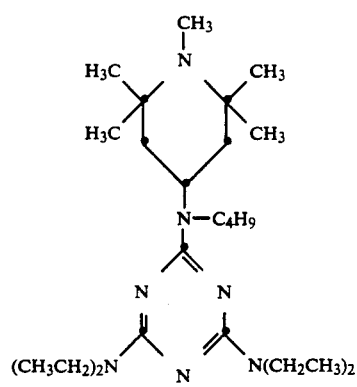
70)
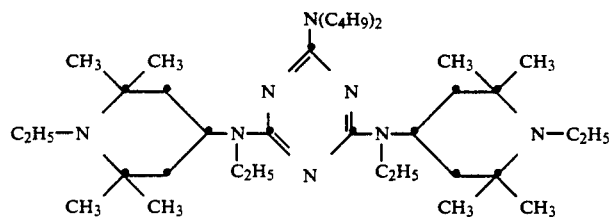
71)
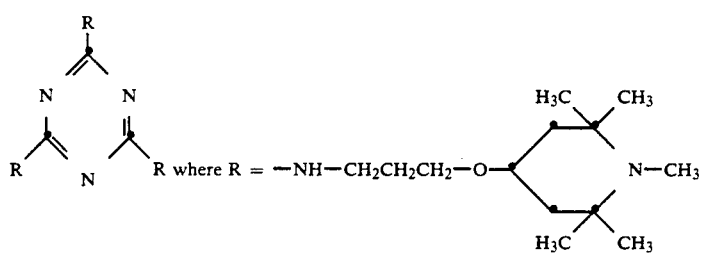
72)
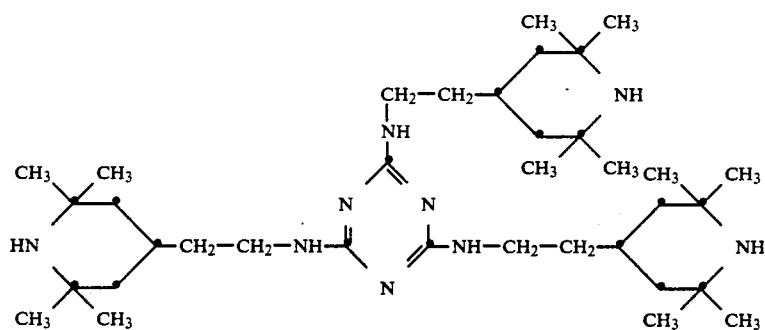
73)
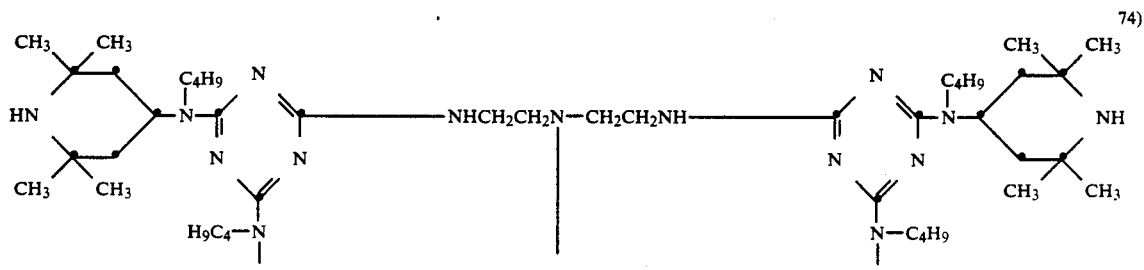
74)

-continued
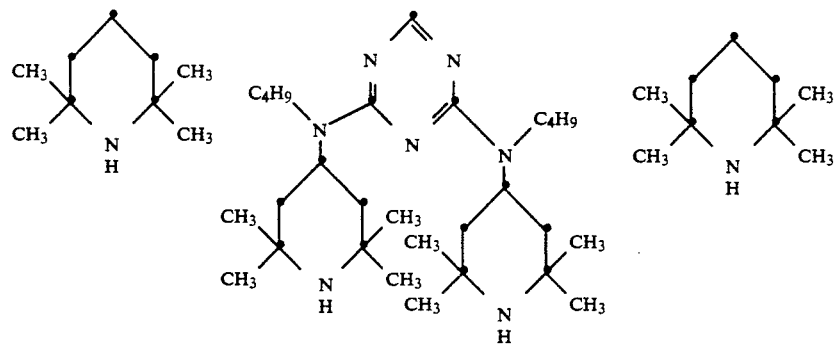
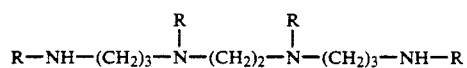  75)
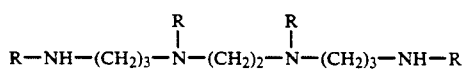  76)
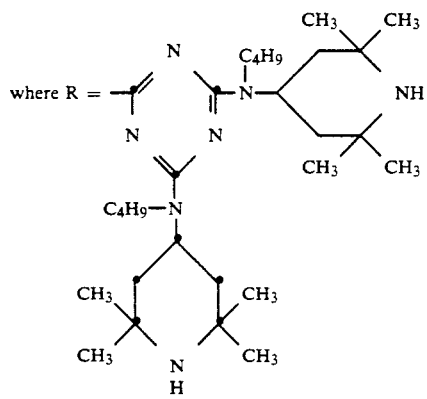
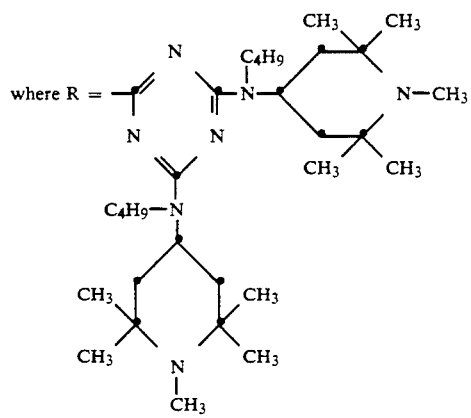
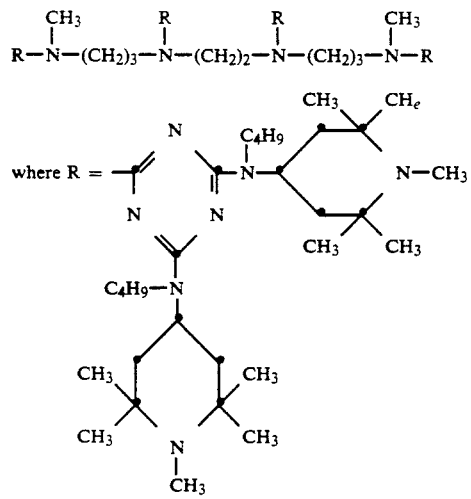  77)
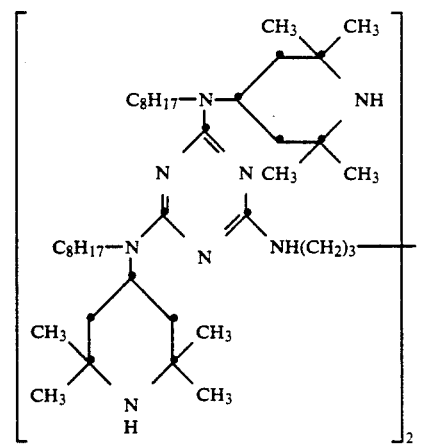  78)

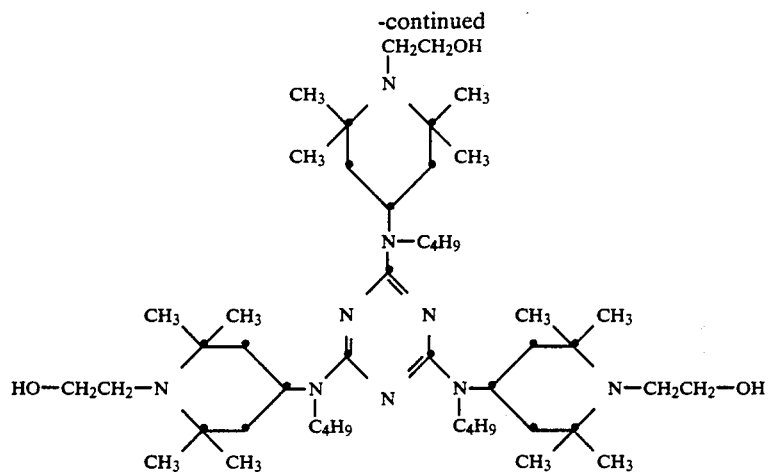

79)

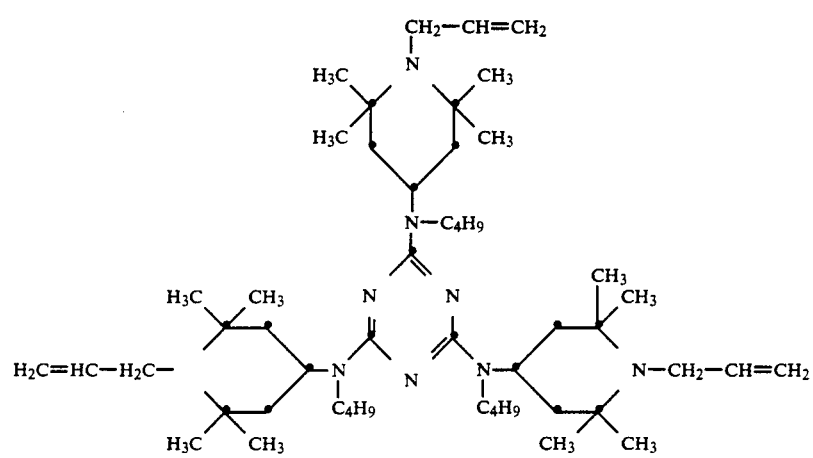

(80)

f) Oligomeric or polymeric compounds whose repeat structural unit contains a 2,2,6,6-tetraalkylpiperidine radical of formula (I), especially polyesters, polyethers, polyamides, polyamines, polyurethanes, polyureas, polyaminotriazines, poly(meth)acrylates, poly(meth)acrylamides and copolymers thereof which contain such radicals.

The compounds of the following formulae are examples of 2,2,6,6-polyalkylpiperidine light stabilizers of this class, m being a number from 2 to about 200:

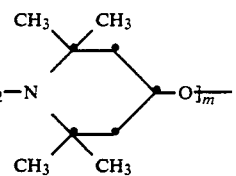

81)

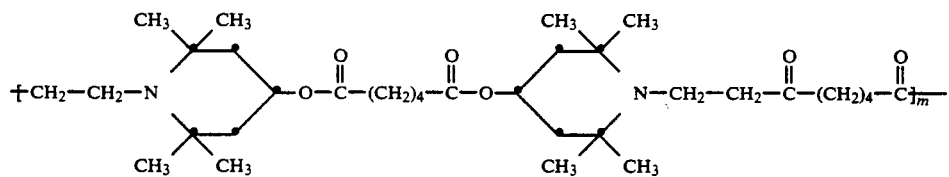

82)

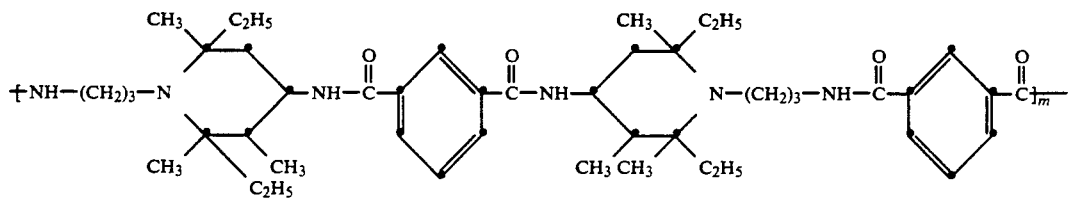

83)

-continued
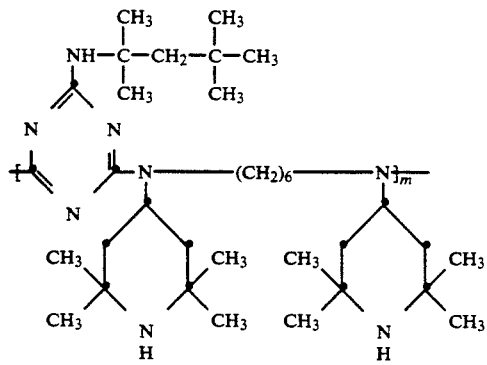 84)
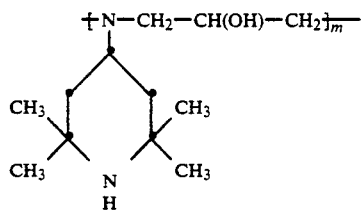 85)
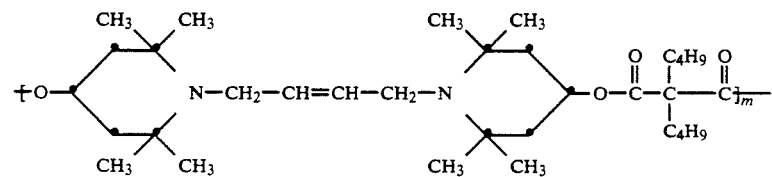 86)
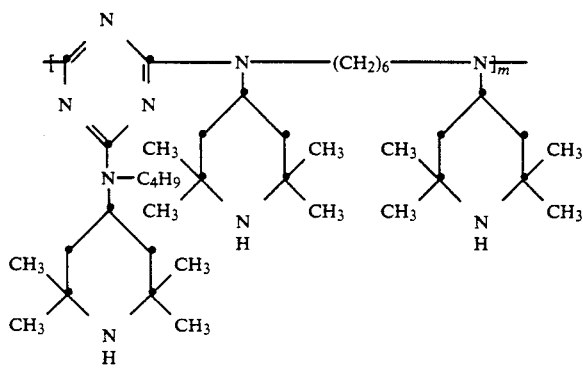 87)
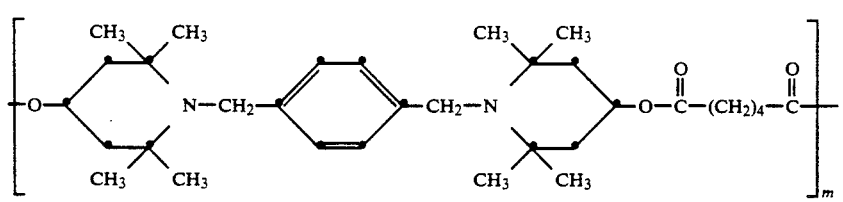 88)
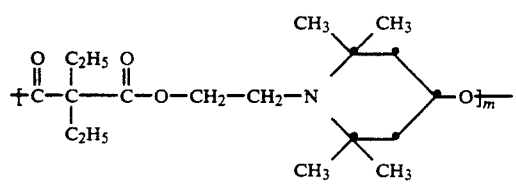 89)
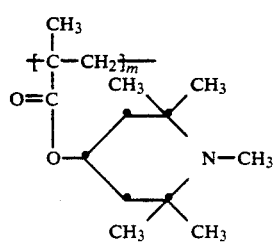 90)

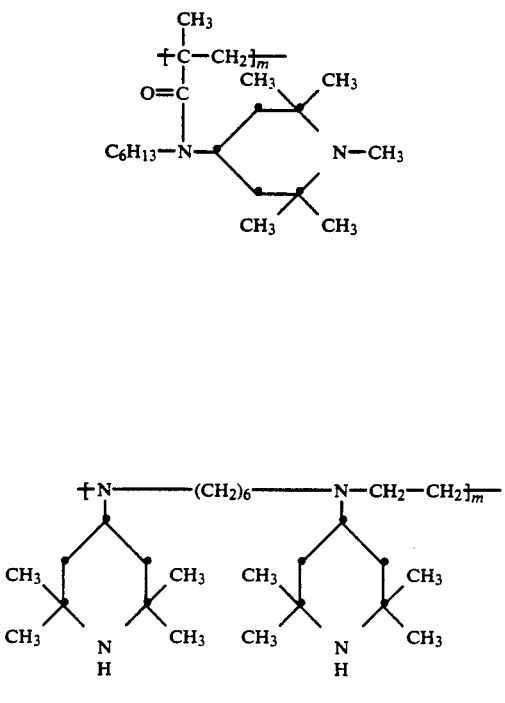

91)

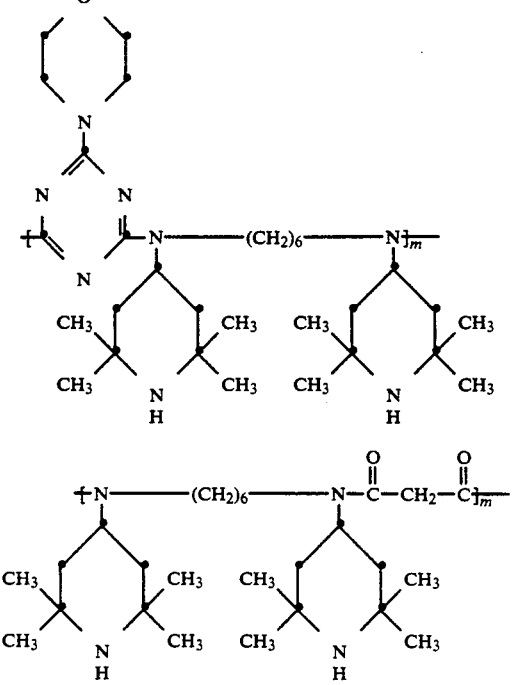

92)

93)

94)

Of these classes of compounds, classses a), d), e) and f) are especially suitable, in particular compounds n°10, 13, 14, 23, 24, 28, 29, 63, 65, 75, 77, 81, 84, 92 and 93.

Apart from the compounds of formula (1) in which X is $CH_2$, NH or S, or apart from the combinations of compounds of formula (1) where $X=CH_2$, NH, O or S with hindered amines, the materials of the invention can also contain other conventional stabilizers and additives, e.g. antioxidants, other light stabilizers, metal passivators, processing stabilizers, nucleating agents, fillers and other additives. Examples of such additional ingredients are:

1. Antioxidants 1.1. Alkylated monophenols, e.g. 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-dicyclopentyl-4-methylpbenol, 2-(a-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1. . Alkylated hydroquinones, e.g. 2,6-di-tert-butyl-4-methoxyphenol, 2,5-di-tert-butylhydroquinone, 2,5-di-tert-amylhydroquinone, 2,6-diphenyl -4-octadecyloxyphenol.

1.3. Hydroxylated thiodiphenyl ethers, e.g. 2,2'-thiobis(6-tert-butyl-4-methylphenol), 2,2'-thiobis(4-octylphenol), 4,4'-thiobis(6-tert-butyl -3-methylphenol), 4,4'-thiobis(6-tert-butyl-2-methylphenol).

1.4. Alkylidenebisphenols, e.g. 2,2'-methylenebis(6-tert-butyl-4-methylphenol), 2,2'-methylenebis(6-tert-butyl-4-ethylphenol), 2,2'-methylene-bis[4-methyl-6-(a-methylcyclohexyl)phenol], 2,2'-methylenebis(4-methyl-6-cyclohexylphenol), 2,2'-methylenebis(6-nonyl-4-methylphenol), 2,2'-methylenebis (4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(a-methylbenzyl)-4-nonylphenol], 2,2'-methylene-bis[6-(a,a-dimethylbenzyl)-4-nonylphenol], 4,4'-methylenebis(2,6-di-tert-butylphenol), 4,4'-methylenebis(6-tert-butyl-2-methylphenol), 1.1-bis(5-tert-butyl-4-hydroxy-2-methylphenyl)butane, 2,6-bis(3-tert-butyl -5-methyl 2-hydroxybenzyl)-4-methylphenol, 1,1,3-tris(5-tert-butyl-4-hydroxy -2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl -phenyl)dicyclopentadiene, bis[2-(3'-tert-butyl-2'-hydroxy-5'-methylbenzyl) -6-tert-butyl-4-methylphenyl] terephthalate.

1.5. Benzy compounds, e.g. 1,3,5-tris(3,5-di-tert-butyl-4-hydroxybenzyl) -2,4,6-trimethylbenzene, bis(3,5-di-tert-butyl-4-hydroxylbenzyl) sulfide, isooctyl 3,5-di-tert-butyl-4-hydroxybenzylmercaptoacetate, bis(4-tert-butyl-3-hydroxy-2,6-dimethylbenzyl) dithiolterephtbalate, 1,3,5-tris(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, e.g. 4-hydroxylauranilide, 4-hydroxystearanilide, 2,4-bis(octylmercapto)-6-(3,5-di-tert-butyl-4-hydroxyanilino)-s-triazine, octyl N-(3,5-di-tert-butyl-4-hydroxyphenyl)carbamate.

1.7. Esters of β-(3,5di-tert-butyl-4-hydroxyphenyl)-propionic acid with monohydric or polyhydric alcohols, e.g. with methanol, octadecanol, hexane-1,6-diol, neopentyl glycol, thiodiet-hylene glycol, diethylene glycol, triethylene glycol, pentaerythritol, tris(hydroxyethyl) isocyanurate, N,N'-bis(hydroxyethyl)oxalodiamide.

1.8. Esters of β-(5-tert-butyl-4-hydroxy-3-methylphenyl)propionic acid with monohydric or polyhydric alcohols, e.g. with methanol, octadecanol, hexane-1,6- diol, neopentyl glycol, thiodiethylene glycol, diethylene glycol, triethylene glycol, pentaerythritol, tris(hydroxyethyl) isocyanurate, N,N'-bis(hydroxyethyl)oxalodiamide.

1.9. Esters of β-(3,5-dicyclohexyl-4-hydroxyphenyl)-propionic acid with monohydric or polyhydric alcohols, e.g. with methanol, octadecanol, hexane-1,6-diol, neopentyl glycol, thiodiethylene glycol, diethylene glycol, triethylene glycol, pentaerythritol, tris(hydroxyethyl) isocyanurate, N,N'-bis(hydroxyethyl)oxalodiamide.

1.10. Amides of β-(3,5-di-tert-butyl-4-hydroxyphenyl)propionic acid, e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles, e.g. the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octyloxy, 3',5'-di-tert-amyl and 3',5'-bis(α,α-dimethylbenzyl) derivatives.

2.2. 2-Hydroxybenzophenones, e.g. the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted or unsubstituted benzoic acids, e.g. 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate.

2.4. Acrylates, e.g. ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate, N-(β-carbomethoxy-β-cyanovinyl)-2-methylindoline.

2.5. Nickel compounds, e.g. nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphospbonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Oxalic acid diamides, e.g. 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)-oxalamide, 2-ethoxy-5-tert-butyl-2'-ethyloxamilide and its mixture with 2-ethoxy-2'-ethyl-5,4'-di-tert-butyloxanilide, mixtures of o- and p-metboxy-disubstituted oxanilides and of o- and p-ethoxy-disubstituted oxanilides.

2.7. 2-(2-Hydroxyphenyl)1,3,5-triazines, e.g. 2,4,6-tris(2-hydroxy-4-octyloxyphenyl)-1,3,5-triazine, 2-(2-hydroxy-4-octyloxyphenyl)-4,6-bis(2,4-dimethylphenyl)-I,3,5-triazine, 2-(2,4-dibydroxyphenyl)-4,6-bis(2,4-dimethylphenyl)-1,3,5-triazine, 2,4-bis(2-hydroxy-4-propoxyphenyl)-6-(2,4-dimethylphenyl)-1,3,5-triazine, 2-(2-hydroxy-4-octyloxyphenyl)-4,6-bis 4-methylphenyl)-1,3,5-triazine, 2-(2-hydroxy-4-dodecyloxyphenyl)-4,6-bis(2,4-dimethylphenyl)-1,3,5-triazine.

3. Metal Passivators, e.g. N,N'-diphenyloxalodiamide, N-salicylal-N'-salicyloylbydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide.

4. Phosphites and phoshonites, e.g. triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol tripbosphite, tetrakis(214-di-tert-butylphenyl)-4,4'-bipbenylene diphosphonite, 3,9-bis(2,4-di-tert-butylphenoxy)-2,4,8,10-tetraoxa-3,9-diphosphaspiro[5,5]undecane.

5. Peroxide scavengers, e.g. esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide, pentaerytbritol tetrakis(β-dodecylmercapto) propionate.

6. Polyamide stabilizers, e.g. copper salts in combination with iodides and/or phosphorus compounds, and salts of divalent manganese.

7. Basic co-stabilizers, e.g. melamine, polyvinylpyrolidone, dicyandiamide, triallyl cyanurate, urea derivatives, hydrazine derivatives, amines, polyamides, polyurethanes, alkali metal and alkaline earth metal salts of higher fatty acids, for example calcium stearate, zinc stearate, magnesium stearate, sodium ricinoleate, potassium palmitate, antimony pyrocatecholate or tin pyrocatecholate.

8. Nucleating agents, e.g. 4-tert-butylbenzoic acid, adipic acid, diphenylacetic acid.

9. Fillers and reinforcing agents, e.g. calcium carbonate, silicates, glass fibres, asbestos, talc, kaolin, mica, barium sulfate, metal oxides and hydroxides, carbon black, graphite.

10. Other additives, e.g. plasticizers, lubricants, emulsifiers, pigments, fluorescent whitening agents, flameproofing agents, antistatic agents, blowing agents.

Organic polymers, especially synthetic polymers, are to be singled out among the organic materials which can be protected according to the invention from damage by light. Thermoplastics and especially lacquer compositions are preferably protected; in the latter case, the polymeric binder in particular is stabilized against the effect of light.

Lacquer compositions or lacquers which contain the compounds of formula (1) can be e.g. pigmented or unpigmented lacquers or metallic lacquers. They can contain an organic solvent or be solvent-free, or they can be water-based lacquers.

The lacquers can contain at least one of the polymers listed above as a binder. The following are examples of lacquers with special binders:

1. Lacquers based on cold-crosslinking or hot-crosslinking alkyd, acrylate, polyester, epoxy or melamine resins or mixtures of such resins, if appropriate with the addition of an acid curing catalyst.
2. Two-component polyurethane lacquers based on acrylate, polyester or polyether resins containing hydroxyl groups and on aliphatic or aromatic polyisocyanates.
3. Single-component polyurethane lacquers based on blocked polyisocyanates which are unblocked during stoving.

4. Two-component lacquers based on (poly)ketimines and aliphatic or aromatic polyisocyanates.
5. Two-component lacquers based on (poly)ketimines and an unsaturated acrylate resin, a polyacetoacetate resin or a methacrylamidoglycolate methyl ester.
6. Two-component lacquers based on polyacrylates containing carboxyl or amino groups and on polyepoxides.
7. Two-component lacquers based on acrylate resins containing anhydride groups and on a polyhydroxyl or polyamino component.
8. Two-component lacquers based on (poly)oxazolidines and acrylate resins containing anhydride groups, unsaturated acrylate resins or aliphatic or aromatic polyisocyanates.
9. Two-component lacquers based on unsaturated polyacrylates and polymalonates.
10. Thermoplastic polyacrylate lacquers based on thermoplastic acrylate resins or externally cross-linking acrylate resins in combination with etherified melamine resins.
11. Lacquer systems based on siloxane-modified acrylate resins.
12. Lacquer systems based on fluorine-modified acrylate resins.

The lacquers can also be radiation-curable lacquers. In this case, the binder consists of monomeric or oligomeric compounds which contain ethylenic double bonds and are converted to a crosslinked high-molecular form by irradiation with actinic light or with electron beams. Said binder is generally a mixture of such compounds.

The lacquers can be applied as one-coat or two-coat lacquers, the stabilizers of the invention preferably being added to the top coat.

The lacquers can be applied to the substrates (metal, plastic, wood etc.) by the conventional processes, for example by coating, spraying, pouring, dipping or electrophoresis. Lacquers which can be applied to motor vehicles (automotive finishes) are especially preferred.

The compounds of formula (1) can be incorporated into lacquers or lacquer compositions, as well as other photosensitive organic materials, by conventional known methods. The amount of UV absorber added depends on the organic material and its stability requirements. In general, 0.01 to 5% by weight, especially 0.02 to 3% by weight, of UV absorber is added, based on the material.

The components of stabilizer combinations can be added to the organic material individually or as a mixture. The compounds of formula (1) and, if desired, other stabilizers are preferably added before or during the shaping of the material in the case of e.g. thermoplastics. However, they can also be added to the starting monomers before or during the polymerization. In the case of lacquer compositions, the stabilizers which can be used according to the invention are mixed especially with the lacquer formulation or parts of the lacquer formulation prior to application.

The compounds of the invention of formula (1) in which X is S, and also the compounds used according to the invention of formula (1) in which X is $CH_2$, NH or O, prove to be effective UV absorbers distinguished by a high fastness to light. They are therefore suitable for the permanent protection of photosensitive organic materials from the harmful effects of light.

The compounds of formula (1) can be prepared by methods known per se. For example, heating a mixture of the compounds of the formulae

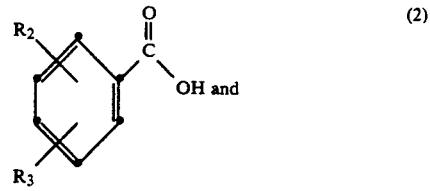

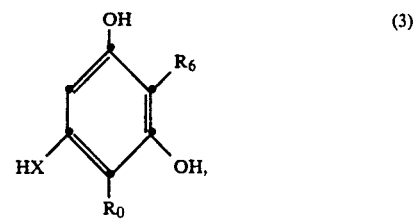

wherein $R_0$, $R_2$, $R_3$ are as defined and X is $CH_2$, NH, O or S, can give the intermediate of the formula

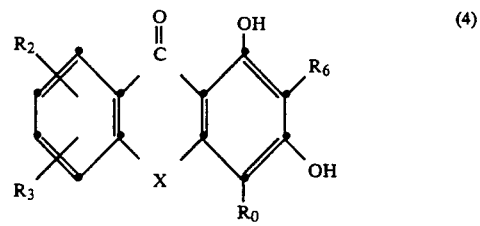

which can be converted to the corresponding compound of formula (1) by reaction with, for example, $R_1$-Cl or $R_1$-Br, wherein $R_1$ is as defined.

The following Examples illustrate the invention in greater detail. Parts or percentages are by weight, unless stated otherwise.

PREPARATORY EXAMPLES

EXAMPLE 1

1-Hydroxy-3-octyloxyxanthone 22.8 g of 1,3-dihydroxyxanthone (prepared according to Grover, J. Chem. Soc. 1955, 3982) are refluxed for 15 hours in 250 ml of methyl ethyl ketone with 15.2 g of $K_2CO_3$ and 21.2 g of 1-bromooctane. After cooling, the salt is filtered off and the methyl ethyl ketone solution is evaporated under vacuum. Crystallization of the residue from heptane gives 1-hydroxy-3-octyloxyxanthone with a melting point of 98° C.

EXAMPLE 2

22.8 g of 1,3-dihydroxyxanthone (prepared according to Grover, J. Chem. Soc. 1955, 3982) are introduced into 300 ml of absolute ethanol. 11.2 g of potassium tert-butylate and then 0.5 g of potassium iodide are added slowly in portions. 12.3 g of ethyl chloroacetate are added dropwise in ca. 15 minutes at room temperature and the reaction mixture is then refluxed for 6 hours. It is poured into 500 ml of water and acidified with 20 ml of glacial acetic acid. The precipitate formed is isolated by suction filtration and dried. Recrystallization from hexane gives the compound of the formula

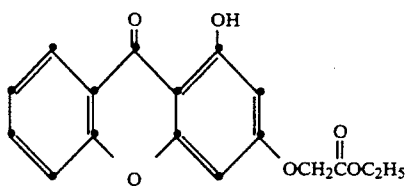

with a melting point of 165° C.

EXAMPLE 3

22.8 g of 1,3-dihydroxyxanthone (prepared according to Grover, J. Chem. Soc. 1955, 3982) are heated to 120° C. in 200 ml of xylene. After the addition of 1.5 g of tetrabutylammonium bromide, 20.5 g of 2-ethylhexyl glycidyl ether are added dropwise in ca. 10 minutes and the reaction mixture is then stirred for 24 hours at 120° C. 5 g of Tansil AC are then added to the reaction solution, which is stirred for 5 minutes at 110° C. and filtered hot. The filtrate is evaporated, the residue is taken up in 300 ml of hexane and the mixture is filtered on 50 g of silica gel. After evaporation, the compound of the formula

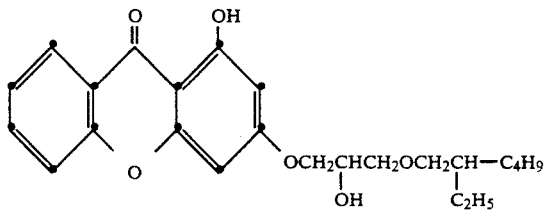

is obtained in the form of a yellowish resin, which crystallizes slowly. The melting point is 56° to 58° C.

APPLICATION EXAMPLE 1

The UV absorbers of the invention are tested in a 2-coat metallic lacquer.

A transparent lacquer of the following composition is prepared:

| | |
|---|---|
| Uracron ® 2263 XB (50%) | 59.2 parts |
| Cymel ® 327 (90%) | 11.6 parts |
| Baysilon ® A (1% in xylene) | 1.0 part |
| Butyl glycol acetate | 5.5 parts |
| Xylene | 19.4 parts |
| Butanol | 3.3 parts |
| | 100.0 parts |

1 part of the compound according to Preparatory Example 1, dissolved beforehand in 10 parts of xylene, is added.

This transparent lacquer is diluted for sprayability with a mixture of xylene (13 parts), butanol (6 parts) and butyl glycol acetate (1 part), sprayed on to a prepared aluminum sheet (coil-coated, automotive filler, metallic silver base lacquer based on polyester/cellulose acetatobutyrate/melamine resin) and stoved at 130° C. for 30 minute is a dry layer thickness of 40 to 50 μm of transparent lacquer. By way of comparison, an aluminum sheet prepared in the same way is coated with the transparent lacquer defined above, except that it is free of UV absorber.

The samples obtained in this way are tested for gloss retention after weathering. The samples stabilized according to the invention have a markedly better weathering stability than the sample without UV absorber.

Lacquers which, apart from said UV absorbers, contain a sterically hindered amine of the formula

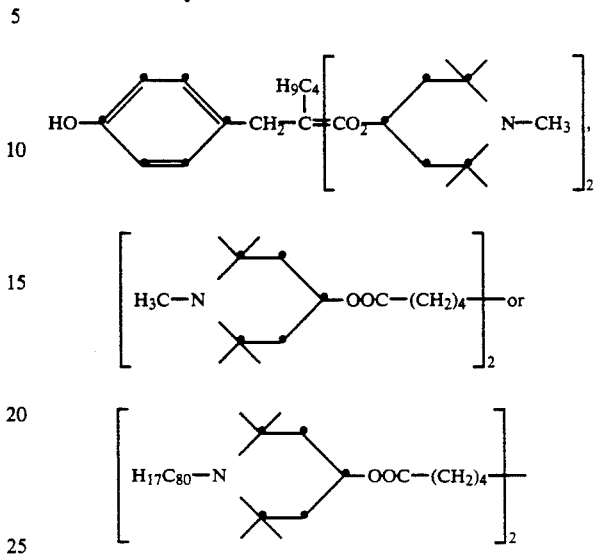

also have comparably good properties.

The results are collated in Table 1 below.

TABLE 1

Evaluation of the gloss retention after weathering according to DIN 67530 (20° gloss)

| UV-absorber | 20° gloss after | | | |
|---|---|---|---|---|
| | 0 | 400 | 800 | 1200 hours |
| none | 86 | 75 | 45 | 16 |
| according to Example 1 | 84 | 78 | 74 | 81 |
| according to Example 2 | 85 | 75 | 68 | 74 |
| according to Example 3 | 86 | 80 | 80 | 80 |
| according to formula (5) | 85 | 73 | 70 | 74 | formula (5)

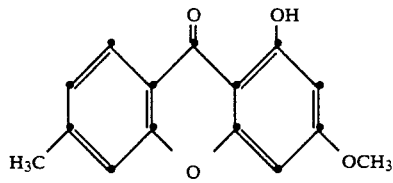

Cycle:
8 hours of UV (UVB-313), 70° C.
4 hours of conditioning, 50° C. (UVCON)

APPLICATION EXAMPLE 2

Application Example 1 is repeated, except that 0.5 part of the compound of the formula

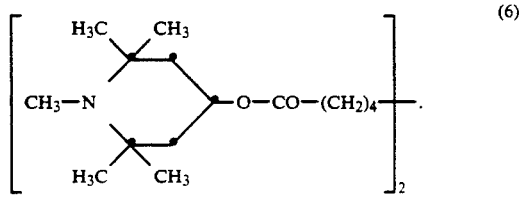

(6)

is used as the additional uV absorber. The results are given in Table 2.

TABLE 2

Evaluation of the gloss retention after weathering according to DIN 67530 (20° gloss)

| UV-absorber | 20° gloss after | | | |
|---|---|---|---|---|
| | 0 | 400 | 800 | 1200 hours |
| none | 86 | 71 | 52 | 36 |
| 1 part according to example 1 + 0.5 part of (6) | 86 | 70 | 61 | 56 |
| 1 part according to example 3 + 0.5 part of (6) | 86 | 74 | 66 | 57 |

Cycle: VDA method C (Xenotest 1200)

We claim:

1. A composition stabilized against the harmful effects of UV radiation which comprises:
   (a) a major amount of a photosensitive organic polymeric material subject to the harmful effects of UV radiation; and
   (b) a minor stabilizing effective amount of a combination of:
   (i) a compound of formula (1)

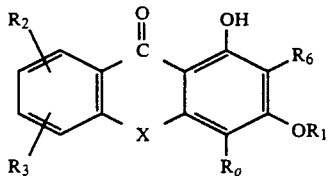

wherein X is —O—,
   $R_0$ is hydrogen or a radical of the formula —($CH_2$)$_n$$CO_2$R, wherein n is 1 or 2 and R is alkyl having 1 to 18 carbon atoms or —$CH_2CH_2O)_m$H wherein m is 1 to 12, $R_1$ is hydrogen, alkyl having 1 to 12 carbon atoms, alkyl having 2 to 18 carbon atoms which is substituted by hydroxyl and/or interrupted by oxygen, alkenyl having 2 to 12 carbon atoms or —$COR_4$, wherein $R_4$ is alkyl having 1 to 12 carbon atoms, alkenyl having 2 to 12 carbon atoms,

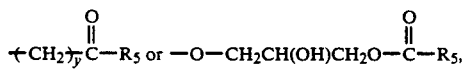

or $R_1$ is —($CH_2$)$_y$O—$COR_5$ wherein $R_5$ is alkyl having 1 to 12 carbon atoms or alkenyl having 2 to 12 carbon atoms and y is 1 to 12,
   $R_2$ and $R_3$ independently of the other are hydrogen, alkyl having 1 to 12 carbon atoms, alkenyl having 2 to 12 carbon atoms, chlorine or —$OR_1$ wherein $R_1$ is as defined above, and
   $R_6$ is hydrogen or alkyl having 1 to 4 carbon atoms, and
   (ii) at least one sterically hindered amine or hydroxyphenylbenzotriazole derivative.

2. A composition according to claim 1 in which $R_0$ is a radical of the formula —$CH_2CH_2CO_2R$, wherein R is alkyl having 1 to 18 carbon atoms or —$CH_2CH_2O)_m$H in which m is 4 to 8.

3. A composition according to claim 1, in which $R_0$ is a radical of the formula —$CH_2CH_2CO_2CH_3$.

4. A composition according to claim 1 in which, in the compound of formula (1) $R_2$ and $R_3$ are hydrogen.

5. A composition according to claim 1 in which, in the compound of formula (1), $R_1$ is hydrogen, alkyl having 4 to 8 carbon atoms, alkyl having 2 to 12 carbon atoms which is substituted by hydroxyl and/or interrupted by oxygen, alkenyl having 4 to 12 carbon atoms or —$COR_4$ in which $R_4$ is alkyl having 4 to 8 carbon atoms.

6. A composition according to claim 5 in which, in the compound of formula (1), $R_1$ is hydrogen or alkyl or alkenyl each having 4 to 8 carbon atoms.

7. A composition according to claim 1 which is a lacquer or a thermoplastic polymer.

8. A composition according to claim 1 where in the compound of formula (1), $R_0$, $R_2$, $R_3$ and $R_6$ are each hydrogen, $R_1$ is —$CH_2CHOHCH_2OCH_2CH(C_2H_5)C_4H_9$ and X is —O—.

9. A composition according to claim 1 wherein the compound of formula (1) is 1-hydroxy-3-octyloxyxanthone.

10. A composition according to claim 1 wherein the compound of formula (1) is 1-hydroxy-3-ethoxycarbonylmethoxyxanthone.

11. A composition according to claim 1 wherein the compound of formula (1) is 6-methyl-1-hydroxy-3-methoxyxanthone.

12. A composition according to claim 1 wherein the sterically hindered amine is bis(1,2,2,6,6-pentamethylpiperidin-4-yl) sebacate.

* * * * *